US008840640B2

(12) United States Patent  (10) Patent No.: US 8,840,640 B2
Pipenhagen et al.  (45) Date of Patent: Sep. 23, 2014

(54) VASCULAR CLOSURE DEVICE HAVING AN IMPROVED PLUG

(75) Inventors: Catherine A. Pipenhagen, Chanhassen, MN (US); William R. Fiehler, Exton, PA (US); Melissa K. Gardner, Mendota Heights, MN (US); Janet L. Jacobsen, Maple Grove, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1335 days.

(21) Appl. No.: 11/967,896

(22) Filed: Dec. 31, 2007

(65) Prior Publication Data

US 2009/0171387 A1 Jul. 2, 2009

(51) Int. Cl.
*A61B 17/03* (2006.01)
*A61B 17/00* (2006.01)

(52) U.S. Cl.
CPC ... *A61B 17/0057* (2013.01); *A61B 2017/00654* (2013.01)
USPC ........................................ 606/213

(58) Field of Classification Search
USPC ........... 606/65, 200, 213–217, 232, 310, 313, 606/326, 327; 604/14–18, 59–64
See application file for complete search history.

(56) References Cited

U.S. PATENT DOCUMENTS

| | | |
|---|---|---|
| 3,405,083 A | 10/1968 | Morrison et al. |
| 4,317,445 A | 3/1982 | Robinson |
| 4,744,364 A | 5/1988 | Kensey |
| 4,890,612 A | 1/1990 | Kensey |
| 5,021,059 A | 6/1991 | Kensey et al. |
| 5,055,410 A | 10/1991 | Blumenthal et al. |
| 5,061,274 A | 10/1991 | Kensey |
| 5,108,421 A | 4/1992 | Fowler |
| 5,192,302 A | 3/1993 | Kensey et al. |
| 5,222,974 A | 6/1993 | Kensey et al. |
| 5,282,827 A | 2/1994 | Kensey et al. |
| 5,290,310 A | 3/1994 | Makower et al. |
| 5,292,332 A * | 3/1994 | Lee ............................... 606/213 |
| 5,304,184 A | 4/1994 | Hathaway et al. |
| 5,306,254 A | 4/1994 | Nash et al. |
| 5,312,435 A | 5/1994 | Nash et al. |
| 5,320,639 A | 6/1994 | Rudnick |
| 5,326,350 A | 7/1994 | Li |
| 5,334,216 A | 8/1994 | Vidal et al. |
| 5,342,393 A | 8/1994 | Stack |
| 5,352,216 A | 10/1994 | Shiono et al. |
| 5,368,601 A | 11/1994 | Sauer et al. |

(Continued)

FOREIGN PATENT DOCUMENTS

| | | |
|---|---|---|
| WO | 03094749 | 11/2003 |
| WO | 2004041122 | 5/2004 |
| WO | 2007044510 | 4/2007 |

*Primary Examiner* — Kathleen Holwerda
(74) *Attorney, Agent, or Firm* — Holland & Hart

(57) ABSTRACT

Various embodiments of a device are shown and disclosed for closing a vascular access puncture site following percutaneous diagnostic or therapeutic interventional procedures. The vascular closure device includes an improved plug that is configured to be positioned adjacent to the hole in the vasculature. The plug may be shaped to prevent the plug from moving away from the hole in the blood vessel due to pulsatile pressure from the blood. In one embodiment, the plug may include a plurality of projections that extend outward from the plug and contact surrounding tissue in the tissue puncture tract to prevent the plug from moving away from the hole in the blood vessel.

18 Claims, 10 Drawing Sheets

(56) References Cited

U.S. PATENT DOCUMENTS

| | | | |
|---|---|---|---|
| 5,370,660 A | 12/1994 | Weinstein et al. | |
| 5,383,896 A | 1/1995 | Gershony et al. | |
| 5,383,897 A | 1/1995 | Wholey | |
| 5,383,899 A | 1/1995 | Hammerslag | |
| RE34,866 E | 2/1995 | Kensey et al. | |
| 5,391,183 A | 2/1995 | Janzen et al. | |
| 5,403,328 A | 4/1995 | Shallman | |
| 5,403,329 A | 4/1995 | Hinchcliffe | |
| 5,405,354 A | 4/1995 | Sarrett | |
| 5,411,520 A | 5/1995 | Nash et al. | |
| 5,417,699 A | 5/1995 | Klein et al. | |
| 5,431,639 A | 7/1995 | Shaw | |
| 5,431,666 A | 7/1995 | Sauer et al. | |
| 5,437,631 A | 8/1995 | Janzen | |
| 5,443,481 A | 8/1995 | Lee | |
| 5,462,561 A | 10/1995 | Voda | |
| 5,486,195 A | 1/1996 | Myers et al. | |
| 5,496,332 A | 3/1996 | Sierra et al. | |
| 5,496,335 A | 3/1996 | Thomason et al. | |
| 5,507,744 A | 4/1996 | Tay et al. | |
| 5,507,758 A | 4/1996 | Thomason et al. | |
| 5,527,322 A | 6/1996 | Klein et al. | |
| 5,531,759 A | 7/1996 | Kensey et al. | |
| 5,545,178 A | 8/1996 | Kensey et al. | |
| 5,549,633 A | 8/1996 | Evans et al. | |
| 5,571,181 A | 11/1996 | Li | |
| 5,591,205 A | 1/1997 | Fowler | |
| 5,593,422 A | 1/1997 | Muijs Van de Moer et al. | |
| 5,601,603 A | 2/1997 | Illi | |
| 5,613,974 A | 3/1997 | Andreas et al. | |
| 5,620,461 A | 4/1997 | Muijs Van De Moer et al. | |
| 5,626,601 A | 5/1997 | Gershony et al. | |
| 5,643,318 A | 7/1997 | Tsukernik et al. | |
| 5,645,566 A | 7/1997 | Brenneman et al. | |
| 5,649,959 A | 7/1997 | Hannam et al. | |
| 5,653,730 A | 8/1997 | Hammerslag | |
| 5,662,681 A | 9/1997 | Nash et al. | |
| 5,665,106 A | 9/1997 | Hammerslag | |
| 5,674,231 A | 10/1997 | Green et al. | |
| 5,676,689 A | 10/1997 | Kensey et al. | |
| 5,681,334 A | 10/1997 | Evans et al. | |
| 5,700,277 A * | 12/1997 | Nash et al. | 606/213 |
| 5,725,498 A | 3/1998 | Janzen et al. | |
| 5,725,551 A | 3/1998 | Myers et al. | |
| 5,728,122 A | 3/1998 | Leschinsky et al. | |
| 5,728,132 A | 3/1998 | Van Tassel et al. | |
| 5,728,133 A | 3/1998 | Kontos | |
| 5,728,134 A | 3/1998 | Barak | |
| 5,741,223 A | 4/1998 | Janzen et al. | |
| 5,746,755 A | 5/1998 | Wood et al. | |
| 5,755,727 A | 5/1998 | Kontos | |
| 5,759,194 A | 6/1998 | Hammerslag | |
| 5,766,183 A | 6/1998 | Sauer | |
| 5,766,206 A | 6/1998 | Wijkamp et al. | |
| 5,782,861 A | 7/1998 | Cragg et al. | |
| 5,792,173 A | 8/1998 | Breen et al. | |
| 5,807,573 A | 9/1998 | Ljusberg-Wahren et al. | |
| 5,810,810 A | 9/1998 | Tay et al. | |
| 5,810,846 A | 9/1998 | Virnich et al. | |
| 5,810,884 A | 9/1998 | Kim | |
| 5,814,065 A | 9/1998 | Diaz | |
| 5,820,631 A | 10/1998 | Nobles | |
| 5,827,299 A | 10/1998 | Thomason et al. | |
| 5,830,130 A | 11/1998 | Janzen et al. | |
| 5,843,124 A | 12/1998 | Hammerslag | |
| 5,853,421 A | 12/1998 | Leschinsky et al. | |
| 5,855,559 A | 1/1999 | Van Tassel et al. | |
| 5,855,585 A | 1/1999 | Kontos | |
| 5,860,990 A | 1/1999 | Nobles et al. | |
| 5,861,004 A | 1/1999 | Kensey et al. | |
| 5,861,005 A | 1/1999 | Kontos | |
| 5,868,762 A | 2/1999 | Cragg et al. | |
| 5,876,411 A | 3/1999 | Kontos | |
| 5,902,311 A | 5/1999 | Andreas et al. | |
| 5,906,631 A | 5/1999 | Imran | |
| 5,910,155 A | 6/1999 | Ratcliff et al. | |
| 5,919,207 A | 7/1999 | Taheri | |
| 5,941,897 A | 8/1999 | Myers | |
| 5,957,952 A | 9/1999 | Gershony et al. | |
| 5,964,782 A | 10/1999 | Lafontaine et al. | |
| 5,976,161 A | 11/1999 | Kirsch et al. | |
| 5,980,539 A | 11/1999 | Kontos | |
| 5,995,502 A | 11/1999 | Fukuda | |
| 5,997,555 A | 12/1999 | Kontos | |
| 6,007,562 A | 12/1999 | Harren et al. | |
| 6,007,563 A | 12/1999 | Nash et al. | |
| 6,017,359 A | 1/2000 | Gershony et al. | |
| 6,024,747 A | 2/2000 | Kontos | |
| 6,033,401 A | 3/2000 | Edwards et al. | |
| 6,033,427 A | 3/2000 | Lee | |
| 6,036,721 A | 3/2000 | Harren et al. | |
| 6,042,601 A | 3/2000 | Smith | |
| 6,045,569 A | 4/2000 | Kensey et al. | |
| 6,048,357 A | 4/2000 | Kontos | |
| 6,048,358 A | 4/2000 | Barak | |
| 6,056,768 A * | 5/2000 | Cates et al. | 606/213 |
| 6,063,085 A | 5/2000 | Tay et al. | |
| 6,071,300 A | 6/2000 | Brenneman et al. | |
| 6,077,279 A | 6/2000 | Kontos | |
| 6,090,130 A | 7/2000 | Nash et al. | |
| 6,110,184 A | 8/2000 | Weadock | |
| 6,120,524 A | 9/2000 | Taheri | |
| 6,126,675 A | 10/2000 | Shchervinsky et al. | |
| 6,136,010 A | 10/2000 | Modesitt et al. | |
| 6,139,556 A | 10/2000 | Kontos | |
| 6,162,192 A | 12/2000 | Cragg et al. | |
| 6,174,322 B1 | 1/2001 | Schneidt | |
| 6,183,496 B1 | 2/2001 | Urbanski | |
| 6,193,670 B1 | 2/2001 | Van Tassel et al. | |
| 6,197,042 B1 | 3/2001 | Ginn et al. | |
| 6,206,895 B1 | 3/2001 | Levinson | |
| 6,228,383 B1 | 5/2001 | Hansen et al. | |
| 6,231,561 B1 | 5/2001 | Frazier et al. | |
| 6,245,080 B1 | 6/2001 | Levinson | |
| 6,398,796 B2 | 6/2002 | Levinson | |
| 6,425,911 B1 | 7/2002 | Akerfeldt et al. | |
| 6,425,924 B1 | 7/2002 | Rousseau | |
| 6,447,513 B1 * | 9/2002 | Griggs | 606/62 |
| 6,508,828 B1 | 1/2003 | Akerfeldt et al. | |
| 6,547,806 B1 | 4/2003 | Ding | |
| 6,569,185 B2 | 5/2003 | Ungs | |
| 6,596,012 B2 | 7/2003 | Akerfeldt et al. | |
| 6,596,014 B2 | 7/2003 | Levinson et al. | |
| 6,682,489 B2 | 1/2004 | Tenerz et al. | |
| 6,695,867 B2 | 2/2004 | Ginn et al. | |
| 6,712,837 B2 | 3/2004 | Akerfeldt et al. | |
| 6,793,938 B2 | 9/2004 | Sankaram | |
| 6,860,895 B1 | 3/2005 | Akerfeldt et al. | |
| 6,890,343 B2 * | 5/2005 | Ginn et al. | 606/213 |
| 6,929,655 B2 | 8/2005 | Egnelov et al. | |
| 7,850,654 B2 | 12/2010 | Belhe et al. | |
| 2002/0082547 A1 | 6/2002 | Deniega et al. | |
| 2003/0158577 A1 | 8/2003 | Ginn et al. | |
| 2003/0171738 A1 | 9/2003 | Konieczynski et al. | |
| 2004/0122349 A1 | 6/2004 | Lafontaine et al. | |
| 2004/0172060 A1 | 9/2004 | Cates et al. | |
| 2004/0176800 A1 * | 9/2004 | Paraschac et al. | 606/213 |
| 2004/0215232 A1 | 10/2004 | Belhe et al. | |
| 2005/0085854 A1 * | 4/2005 | Ginn | 606/213 |
| 2005/0107750 A1 | 5/2005 | Barongan | |
| 2005/0107826 A1 | 5/2005 | Zhu et al. | |
| 2005/0149116 A1 | 7/2005 | Edwards et al. | |
| 2005/0149117 A1 | 7/2005 | Khosravi et al. | |
| 2005/0228443 A1 | 10/2005 | Yassinzadeh | |
| 2006/0100664 A1 * | 5/2006 | Pai et al. | 606/214 |
| 2007/0020228 A1 | 1/2007 | Williams | |
| 2007/0059350 A1 | 3/2007 | Kennedy et al. | |
| 2007/0060895 A1 | 3/2007 | Sibbitt et al. | |
| 2007/0270904 A1 | 11/2007 | Ginn | |

* cited by examiner

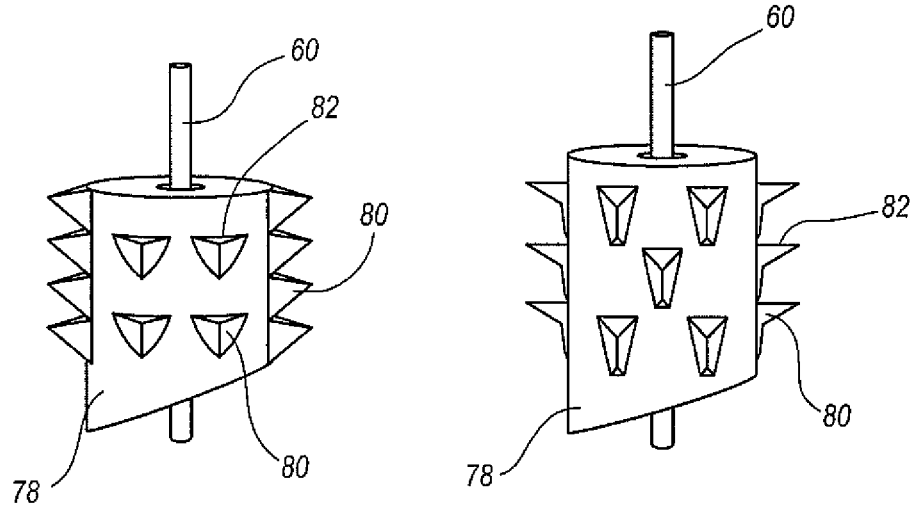
FIG. 9          FIG. 10
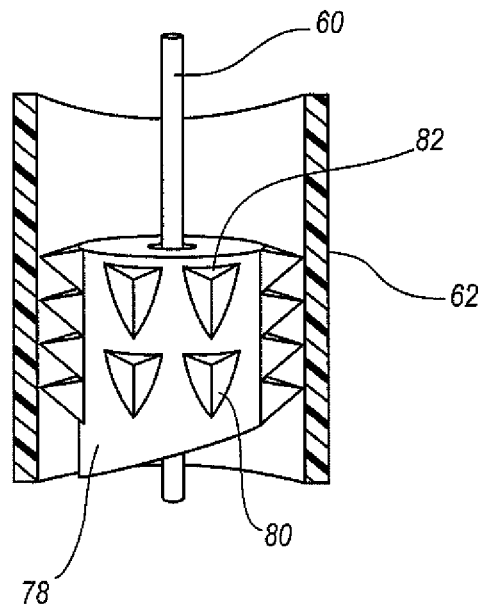
FIG. 11

VASCULAR CLOSURE DEVICE HAVING AN IMPROVED PLUG

CROSS-REFERENCE TO RELATED PATENT APPLICATIONS

U.S. patent application Ser. No. 11/842,509, entitled "Extra-Vascular Sealing Device and Method," filed on 21 Aug. 2007, is hereby incorporated by reference herein in its entirety. In the event of a conflict, the subject matter explicitly recited or shown herein controls over any subject matter incorporated by reference. All definitions of a term (express or implied) contained in any of the subject matter incorporated by reference herein are hereby disclaimed. The paragraphs shortly before the claims dictate the meaning to be given to any term explicitly recited herein subject to the disclaimer in the preceding sentence.

BACKGROUND

Catheter based diagnostic and interventional procedures such as angiograms, balloon angioplasty, stenting, atherectomy, thrombectomy, device placement, etc., are commonly employed to treat patients with vascular obstructions or other abnormalities accessible through the vasculature of the human body. Such interventions are less traumatic to the body than previous surgical interventions and therefore are growing in use.

To gain access to the vasculature, the Seldinger technique is commonly employed. This involves placing a small gauge hollow needle through the skin at about a 30 degree angle to intersect the desired vessel, commonly, but not always, the femoral artery in the groin area. The needle is known to have punctured the vessel wall when blood exits the needle at the proximal end. A guidewire is inserted through the needle into the vessel and the needle is removed. A dilator and introducer sheath are advanced together over the guidewire through the skin and into the vessel. The dilator has a lumen that is sized to receive the guidewire and has a tapered distal end. The introducer sheath has a lumen that is sized to snugly receive the dilator. The size of the introducer sheath is selected (typically 5-8 Fr) to accommodate the catheters anticipated to be used in the procedure. Once the pathway from the outside of the body to the vessel has been established, the dilator and guidewire are removed leaving the introducer sheath in place. A self sealing stretchable valve at the proximal end of the introducer sheath minimizes blood loss during the procedure.

Following the procedure and after all of the catheters and guidewires have been removed from the body, the introducer sheath is removed from the artery. Historically, this has been done by exerting manual pressure on the vessel upstream from the access site to lower blood pressure while the introducer sheath was removed. Once removed, manual pressure is applied directly to the skin above the access puncture for about thirty minutes to inhibit blood loss until the body's natural clotting process sealed the puncture. This technique is generally considered unsatisfactory because it is uncomfortable for the patient and requires a significant amount of nursing staff time.

Sealing the artery by manual compression is rapidly being replaced by medical devices designed to provide a vascular puncture seal in less than five minutes. These devices are intended to be effective and easy to use by medical personnel. The devices range from mechanical suturing devices to collagen plugs, vascular clips, staples, and use of adhesives and sealants. These various approaches have had varying degrees of success and ease of use.

One of the more commonly used devices for closing vessel punctures achieves hemostasis at the vessel puncture site by closing the puncture with an absorbable intra-vessel (e.g., intra-arterial) anchor and an extra-vessel (e.g., extra-arterial) collagen sponge. The anchor and collagen are held together with a self tightening suture loop and slip knot, which, when tightened, sandwiches the puncture hole between the anchor and the collagen sponge. The device is easy to use and the bio-absorbable anchor, collagen and suture sandwich seals the vessel quickly, is more comfortable for the patient, saves valuable nurse time, and allows early patient ambulation.

Although such collagen devices can be highly effective, a substantial number of punctures in, for example, the femoral artery, may cause the patient to be ineligible to use such a device. Factors that may prevent use of this device include presence of peripheral vascular disease, poor needle stick location (too high or too low), or small vessel size which interferes with anchor placement and prevents proper seating of the anchor against the arterial wall.

In an effort to overcome some of these problems, vascular closure devices have been developed that deposit a plug outside the vessel with no component inside the vessel. Such devices may generally require, however, consistently placing the plug near the arterial wall. Unfortunately, these devices suffer from a number of drawbacks. For example, the pressure exerted on the plug can cause the plug to move away from the hole in the vessel resulting in a hemotoma or other complication at the puncture site. Also, the plug may not seal the puncture tract/hole in the blood vessel sufficiently to prevent leakage.

Accordingly, it would be desirable to provide an improved vascular closure device or vascular sealing device that is easy to use, seals quickly and securely, and leaves no component in the blood vessel. A number of embodiments of such improved vascular closure devices are shown and described herein.

SUMMARY

Various embodiments of vascular closure devices are shown and described herein. The vascular closure devices are, generally speaking, hemostatic devices intended to stop bleeding by closing vascular access puncture sites following percutaneous diagnostic or therapeutic procedures. It should be appreciated that the vascular closure devices shown and described herein may be used to close any puncture in any blood vessel although the vascular closure devices are most commonly used to close arteriotomies. It should also be appreciated that the closure devices may be used to close punctures or holes in other bodily vessels.

The vascular closure devices may include an improved plug that is configured to be deployed adjacent to the hole in the blood vessel. The plug may be shaped to prevent the plug from being pushed away from the hole by the pulsatile pressure of the blood in the blood vessel. In one embodiment, the plug may include a plurality of projections that are configured to contact the surrounding tissue in the puncture tract to prevent the plug from moving away from the blood vessel. In another embodiment, the plug may include a plurality of barbs that are configured to contact the surrounding tissue in the puncture tract to prevent the plug from moving away from the blood vessel.

According to one embodiment, a method of closing a hole in a blood vessel comprises locating a wall of the blood vessel adjacent to the hole and positioning a plug outside of the blood vessel and adjacent to the hole, the plug being shaped to prevent the plug from moving away from the blood vessel. The plug may be bioabsorbable and may have an appreciably stable shape in the presence of bodily fluids. According to another embodiment, a method of closing a hole in a blood vessel comprises positioning a plug outside of the blood vessel to close the hole in the blood vessel. According to another embodiment, a method of closing a hole in a blood vessel comprises positioning a plug outside of the blood vessel to close the hole in the blood vessel. The plug may include a plurality of projections that are configured to contact surrounding tissue to prevent the plug from moving away from the blood vessel.

According to another embodiment, a vascular closure device comprises a vessel locating member configured to be inserted through a hole in a blood vessel to locate the position of a wall of the blood vessel that is adjacent to the hole and a plug configured to be deployed outside of the blood vessel adjacent to the hole, the plug being shaped to prevent the plug from moving away from the blood vessel. The plug may be bioabsorbable and may have an appreciably stable shape in the presence of bodily fluids. According to another embodiment, a vascular closure device comprises a vessel locating member configured to locate a wall of a blood vessel that is adjacent to a hole in the blood vessel and a plug configured to be deployed outside of the blood vessel adjacent to the hole in the blood vessel, the plug being shaped to prevent the plug from moving away from the blood vessel, and a sealing material configured to be deployed adjacent to the plug, the sealing material being positioned outside of the blood vessel. The plug may be bioabsorbable.

The foregoing and other features, utilities, and advantages of the subject matter described herein will be apparent from the following more particular description of certain embodiments as illustrated in the accompanying drawings.

DRAWINGS

FIGS. 9-10 show perspective views of additional embodiments of plugs that may be used with the vascular closure device.

FIG. 11 shows the plug from FIG. 9 positioned in the closure sheath.

DETAILED DESCRIPTION

Figure 1:
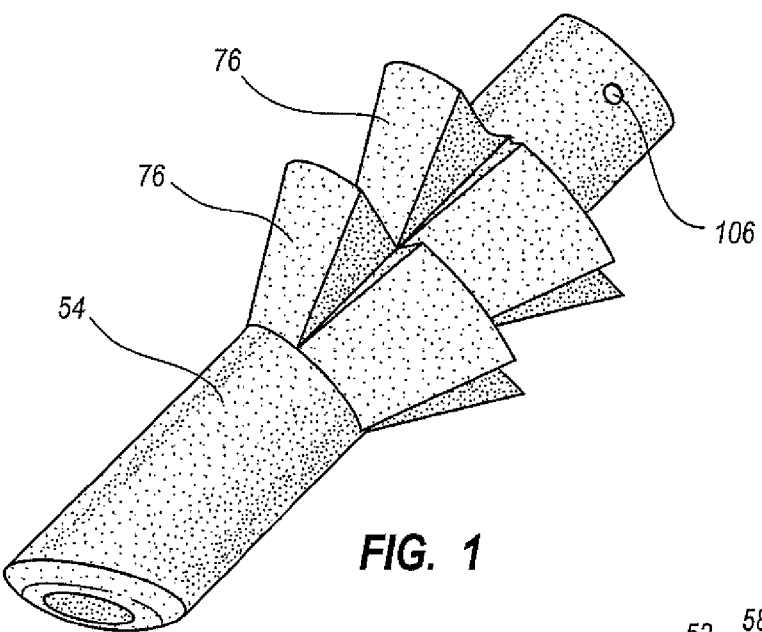
FIG. 1 shows a perspective view of one embodiment of an improved plug for use with a vascular closure device.

A number of embodiments of vascular closure devices are shown and described herein. The vascular closure devices may be used to close a hole or puncture in a blood vessel such as an arteriotomy. The vascular closure devices are hemostatic devices that may be used to stop bleeding from vascular puncture sites following percutaneous diagnostic or therapeutic procedures.

The vascular closure devices may be configured to deploy one or more plugs outside of the blood vessel adjacent to the hole. The plug blocks the hole in the blood vessel and/or the puncture tract to stop the bleeding. In one embodiment, the plug is configured to prevent it from moving away from the hole in the blood vessel due to the pulses in the blood pressure. For example, the plug may be shaped to allow the plug to move toward the blood vessel and prevent or impede the plug from moving away from the blood vessel. The plug may include a plurality of projections or barbs that extend outward from the plug to contact the surrounding tissue to prevent the plug from moving away from the blood vessel. In one embodiment, the plug may be bioabsorbable (e.g., the plug may include PGA materials, PLA materials, or combinations thereof). The plug may also be configured to hold its shape in the presence of bodily fluids.

In another embodiment, the plug may be deployed with and/or coupled to a sealing material such as protein-based sealing materials (e.g., collagen, fibrinogen, thrombin, and the like) or lipid based sealing materials (e.g., glycerol monooleate, and the like). The protein based sealing materials may be configured to expand or swell in the presence of blood to assist in sealing the hole in the blood vessel. The lipid based sealing materials may have a melting point that is near and/or slightly below body temperature. The lipid material may be in solid form in the device, then melt to a liquid or semi-liquid (e.g., gel) form when the device is injected into the patient. When the lipid material contacts bodily fluids, it absorbs the body fluids and changes to a cubic phase material which expands in the puncture tract to close the hole in the blood vessel. In one embodiment, the vascular closure devices may be considered extra-vascular closure devices because the devices do not leave any components in the blood vessel.

It should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

Before describing the particular embodiments of the vascular closure devices, it should be appreciated that the features, advantages, characteristics, etc. described or shown in connection with one of the embodiments may be applied to or combined with any other embodiment to form an additional embodiment unless noted otherwise. Thus, the various embodiments may be modified in a variety of ways to produce many additional embodiments.

Figure 2:
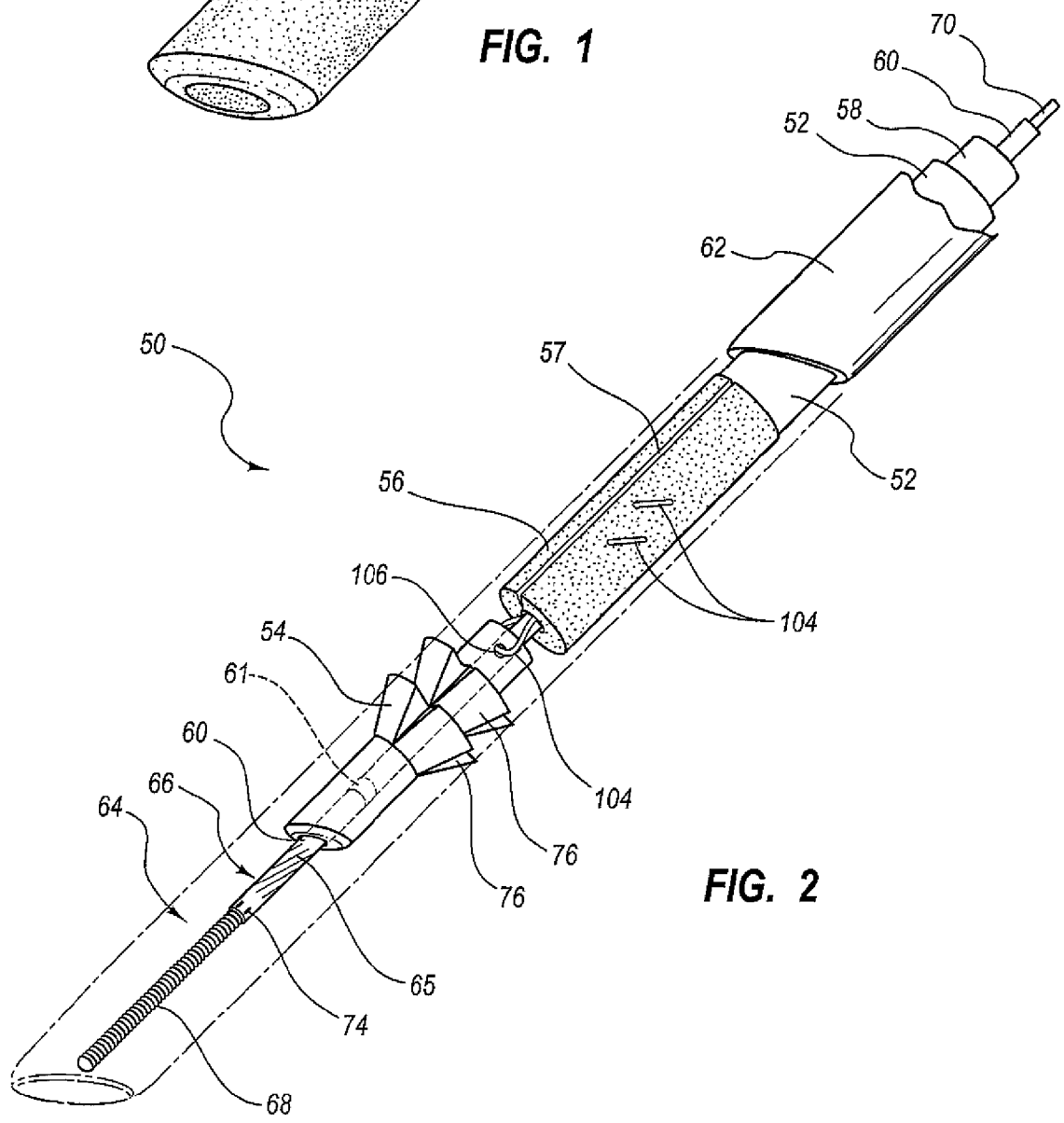
FIG. 2 shows a perspective view of the distal end of a vascular closure device that includes the improved plug from FIG. 1.

Referring to FIGS. 1-2, one embodiment of a vascular closure device 50 is shown that may be used to close and/or seal a hole or puncture in a blood vessel such as an arteriotomy. The vascular closure device 50 includes a carrier tube or carrier member 52, a plug or anchor 54, a sealing material 56, a tamper tube or tamper member 58, and a vessel locator tube or vessel locator portion 60. The vessel locator tube 60 extends through the plug 54, sealing material 56, and the tamper tube 58. The tamper tube 58 is positioned inside the carrier tube 52, and the carrier tube 52 is sized to fit within a closure sheath 62. A vessel locating member 66 and a spring 68 are positioned at a distal end 64 of the vascular closure device 50.

The vessel locator tube 60 and the vessel locating member 66 are generally used to determine the position of the blood vessel as part of the process of closing the hole. The vessel locator tube 60 includes a core wire or guide wire 70 that extends from a proximal end to a distal end 64 of the vascular closure device 50. The spring 68 (e.g., coiled stainless steel spring) is coupled to the distal end of the vessel locator tube 60 and surrounds the core wire 70. The spring 68 may be coupled to the vessel locator tube 60 using any suitable fastening mechanism or technique such as, for example, brazing, soldering, or epoxy adhesive. The distal end of the core wire 70 where it travels through the spring 68 is tapered or reduced in diameter to make the distal end 64 of the vascular closure device 50 more flexible. The distal end of the core wire 70 is coupled to the distal end of the spring 68. Both the core wire 70 and the spring 68 are configured to be atraumatic to prevent the distal end 64 of the vascular closure device 50 from puncturing or damaging the blood vessel.

The vessel locator tube 60 also includes a vessel locating member 66. The vessel locating member 66 is positioned at the distal end of the vessel locator tube 60. The vascular closure device 50 is configured so that when it is inserted into the puncture tract the vessel locating member 66 is positioned inside the blood vessel. In the embodiment shown in FIG. 3, the vessel locating member 66 includes a plurality of strut members 72 formed by making a series of cuts 65 around the vessel locator tube 60 in a spiral pattern. The cuts may be made using a laser or any other suitable device or technique. In one embodiment, the vessel locating member 66 may be configured as described in U.S. Patent Application Publication No. 2006/0196137, entitled "Tissue Anchor Apparatus," filed on 23 Feb. 2006, which is incorporated herein by reference in its entirety.

Figure 3:
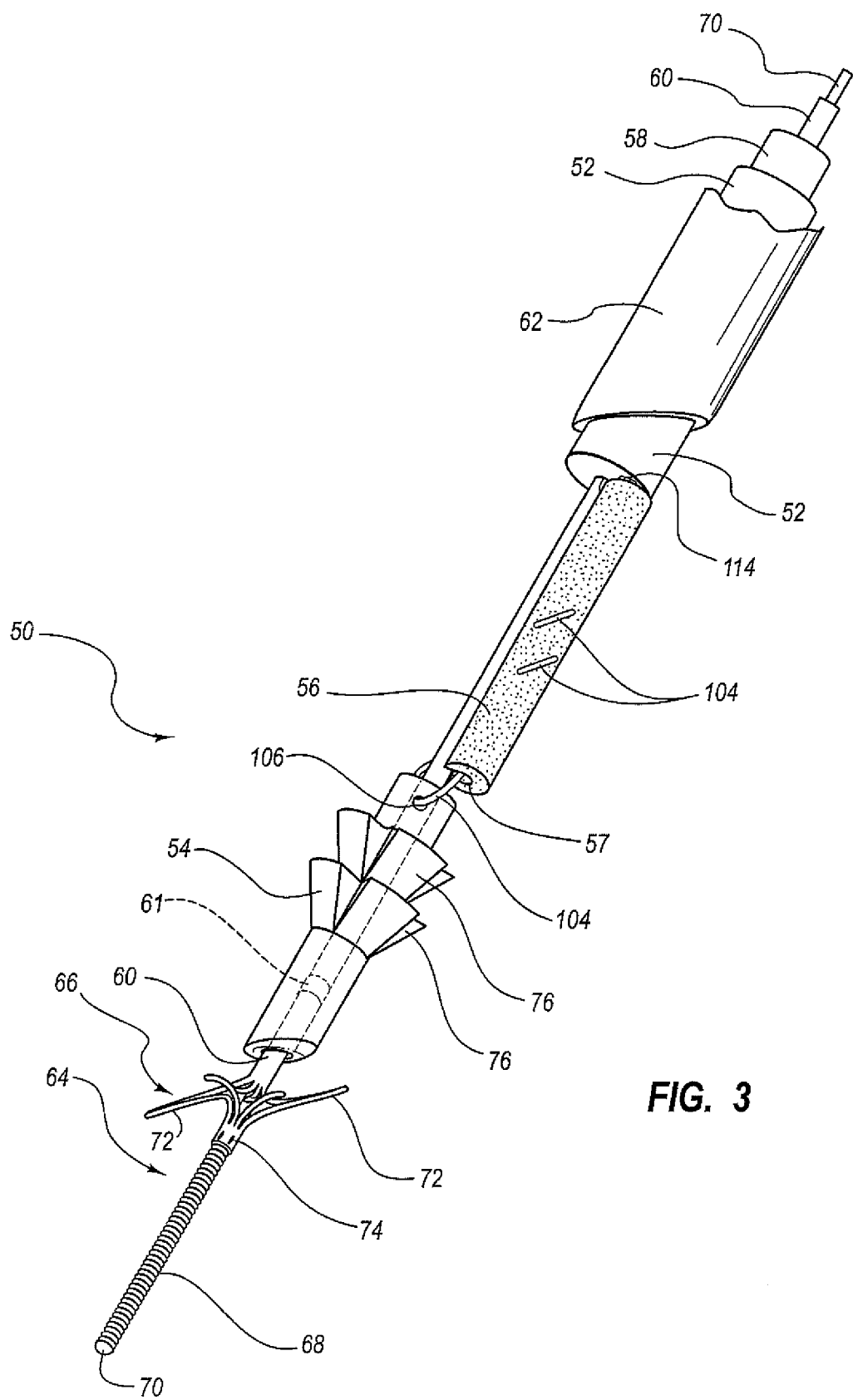
FIG. 3 shows a perspective view of the distal end of a vascular closure device including a vessel locating member that is in an expanded configuration.

The vessel locating member 66 may be configured to move between the contracted configuration shown in FIG. 2 and the expanded configuration shown in FIG. 3. This allows the vessel locating member 66 to be inserted into the blood vessel, expanded, and then moved into contact with the interior wall of the blood vessel adjacent to the hole.

Figure 6:
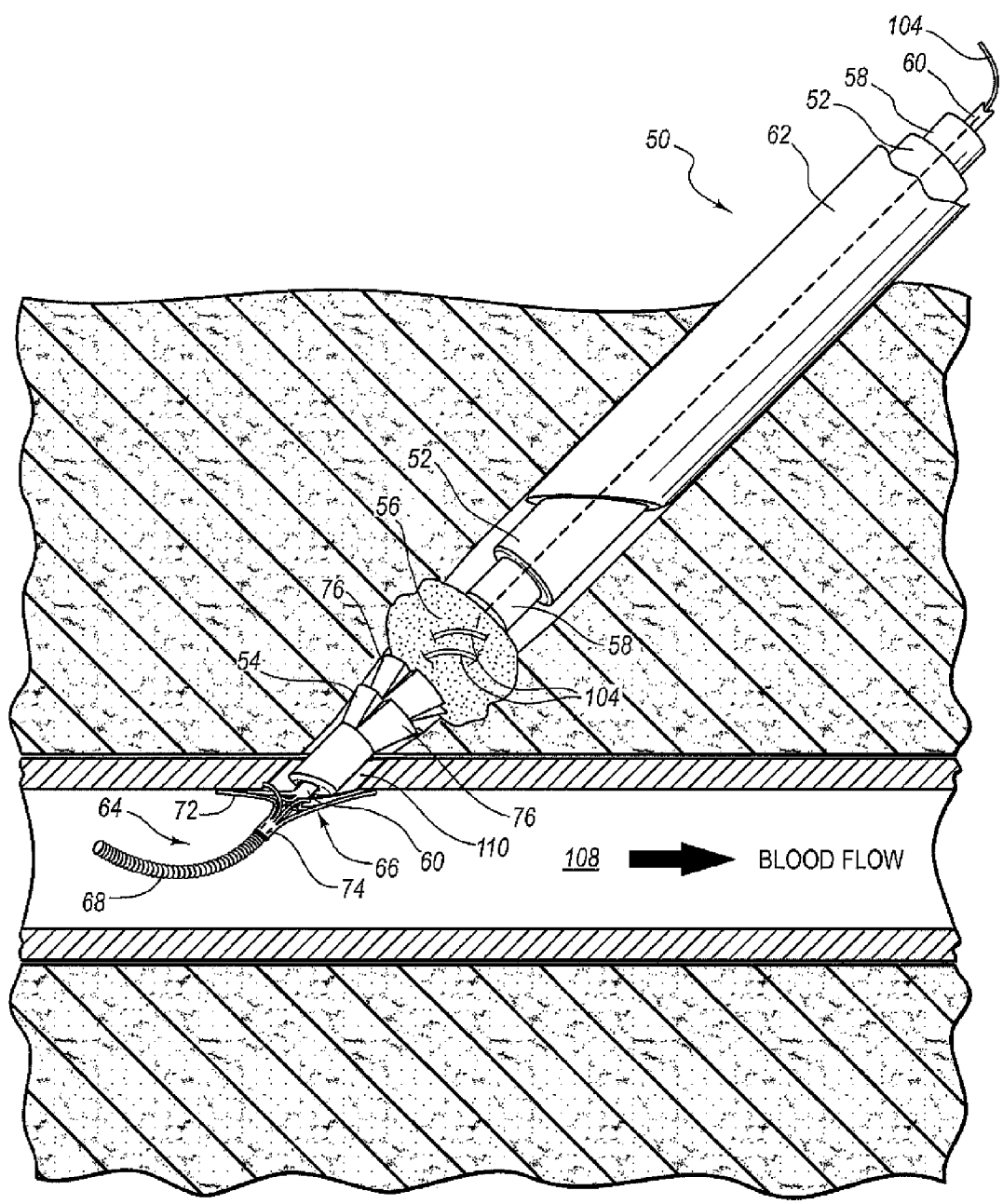
FIG. 6 shows the vascular closure device with the sealing material being tamped with a tamper tube.

The vessel locating member 66 moves between the expanded configuration and the contracted configuration as follows. The core wire 70 is coupled to the vessel locator tube 60 at a position 74 that is distal to the vessel locating member 66. The vessel locating member 66 may be expanded by moving the core wire 70 proximally. Proximal movement of the core wire 70 exerts a compressive force on the vessel locator tube 60 that causes the strut members 72 to deflect outwardly. In one embodiment, the strut members 72 bow and twist as they deflect outwardly. The result, shown in FIG. 6, is that the strut members 72 form a plurality of petal shaped vessel locators that extend radially outward from the vessel locator tube 60.

The vessel locating member 66 may be moved back to the contracted configuration shown in FIG. 2 by moving the core wire 70 in a distal direction to its original position. Distal movement of the core wire 70 exerts a tension force on the vessel locator tube 60 that causes the strut members 72 to straighten and contract or collapse so that the strut members 72 are again in line with the vessel locator tube 60.

In one embodiment, the core wire 70 may be coupled to a handle of the vascular closure device 50 in a way that allows the core wire 70 to be moved back and forth as explained. For example, the vascular closure device 50 may be configured similarly to the vascular closure device referred to in the first paragraph of the specification so that the core wire 70 moves proximally and distally by moving an actuation member proximally and distally.

As explained above, the cuts 65 in the wall of the vessel locator tube 60 may be configured so that the strut members 72 of the vessel locating member 66 form a plane that is not perpendicular to the vessel locator tube 60 as shown in FIG. 3. This may be desirable to create more uniform contact between the vessel locating member 66 and the interior wall of the blood vessel. Since the puncture tract is usually at a 30-45 degree angle relative to the blood vessel, the plane formed by the vessel locating member 66 may also be at an approximately 30-45 degree angle relative to the vessel locator tube 60. When the vessel locating member 66 is in the blood vessel, the vessel locating member 66 may be roughly parallel to the interior wall of the blood vessel just before the vessel locating member 66 contacts the interior wall.

It should be appreciated that the configuration of the vessel locating member 66 can be modified in any of a number of ways. For example, the vessel locating member 66 may be configured to be perpendicular to the vessel locator tube 60. In another embodiment, the vessel locating member 66 may include an inflatable balloon (e.g., inflated with a fluid such as saline solution, carbon dioxide, etc., dispensed from a syringe or other device or container).

It should be appreciated that the vessel locator tube 60 and any of the other components of the vessel locator tube 60 may be made of any suitable material such as metal, plastics, or composites. Since the vascular closure device 50 is a medical device, the materials used may also be medical grade (medical grade metals, plastics, or composites). In one embodiment, the vessel locator tube 60 and the core wire 70 may be made of metals such as stainless steel or memory shape metals such as nitinol, and the like. In another embodiment, the vessel locator tube 60 may be made of a memory shape material such as nitinol (e.g., nitinol hypotube) to allow the vessel locating member 66 to repeatedly expand and contract. In yet another embodiment, the core wire 70 may be a stainless steel wire.

The plug 54 may be positioned at a predetermined distance in the proximal direction from the vessel locating member 66. The distance between the plug 54 and the vessel locating member 66 is selected so that when the vessel locating member 66 is positioned against the interior wall of the blood vessel, a set of projections 76 (described in further detail below) of the plug 54 is positioned just outside of the hole in the blood vessel and a distal end of the plug 54 is positioned within the hole in the blood vessel (see FIGS. 5 and 6). The distal end of the plug 54 may be shaped to be at least substantially flush with the interior wall of the blood vessel as shown in the FIGS. Typically, the distal end of the plug 54 is angled to the same degree as the introducer sheath 62.

The plug 54 is slidably received by the vessel locator tube 60. A marker band 61 is coupled to the vessel locator tube 60 to prevent proximal movement of the plug 54 as it is inserted into the puncture tract. This marker band 61 also prevents proximal movement of the plug 54 during suture take up and removal of the device and assures fixed distance between the locating member 66 and the plug 54. As shown in FIG. 2, the marker band 61 is received inside the plug 54 until it reaches an area where the internal diameter of the plug 54 is smaller than the marker band 61. At this point, the marker band 61 prevents the plug 54 from moving further in the proximal direction. The marker band may be fixed to the vessel locator tube 60 in any of a number of suitable ways such as brazing or with adhesives.

The plug 54 shown in FIG. 1 includes a plurality of projections or barbs 76 that extend outward and are tapered backwards from the distal end of the plug 54 to prevent the plug 54 from moving away from the blood vessel when the plug 54 is deployed adjacent to the hole in the blood vessel. The tapered shape of the projections 76 allow the plug 54 to move distally through the tissue tract but prevent the plug 54 from moving proximally in the tissue tract.

The projections 76 may be made of a resilient material (e.g., elastomeric material) that allows the projections to be compressed inward when the plug 54 moves through the puncture tract in a distal direction. However, when a tensile force is applied to the plug 54 in the proximal direction, the projections 76 may expand and engage the surrounding tissue to prevent proximal movement of the plug 54. The projections 76 prevent the plug 54 from being pushed away from the hole in the blood vessel by the pressure pulses of the blood, thus preventing a hematoma or surface bleeding.

It should be appreciated that the projections 76 may take any suitable form to prevent the plug 54 from moving away from the hole in the blood vessel. For example, another embodiment of a plug 78 is shown in FIGS. 9-11 that includes a plurality of projections or barbs 80 that have a sloped pyramid shape. The projections 80 slope outward and backwards in a proximal direction so that the proximal side of the projections 80 is a flat surface 82 that extends outward almost perpendicular to the plug 78. The flat surface 82 is configured to engage the tissue in the tissue tract to prevent the plug 78 from moving away from the hole in the blood vessel.

Figures 12, 13:
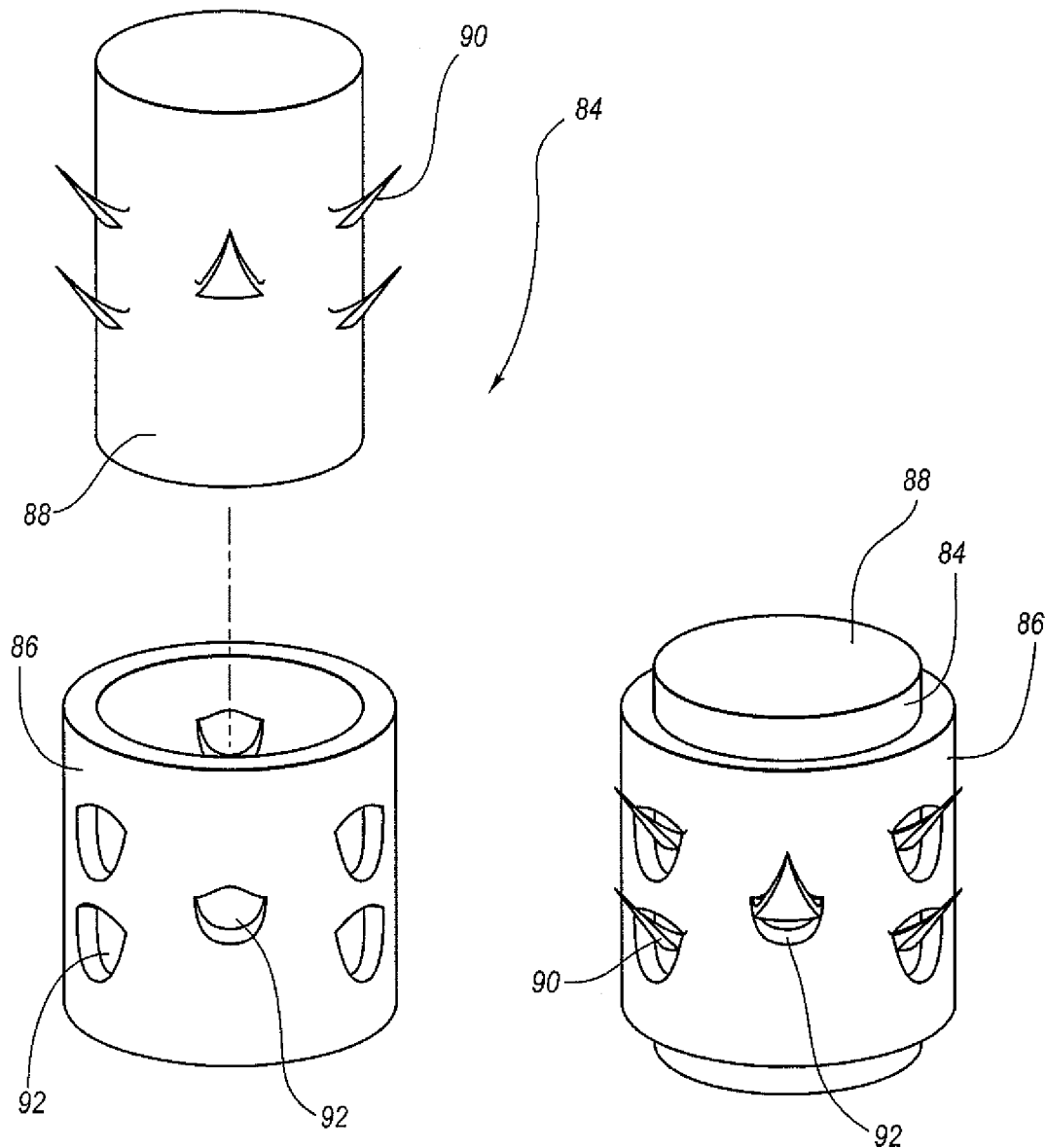
FIGS. 12-15 show perspective views of additional embodiments of plugs that may be used with the vascular closure device.

Another embodiment of a plug 84 is shown in FIGS. 12-13. In this embodiment, the plug 84 includes a sleeve 86 and a core or main body 88 that fits inside the sleeve 86. The core 88 includes a plurality of resilient or flexible projections or barbs 90. The sleeve 86 includes a plurality of corresponding holes 92. The core 88 is configured to slide between a first configuration where the projections 90 are pressed snugly between the wall of the sleeve 86 and the core 88 and a second configuration where the projections 90 are configured to extend outward through the holes 92 in the sleeve 86. The plug 84 may be moved between the first configuration and the second configuration by selectively moving the core 88 further distally into or proximally out of the sleeve 86 or the core can be twisted (i.e., rotated about its axis) relative to the sleeve 86.

Figure 14:
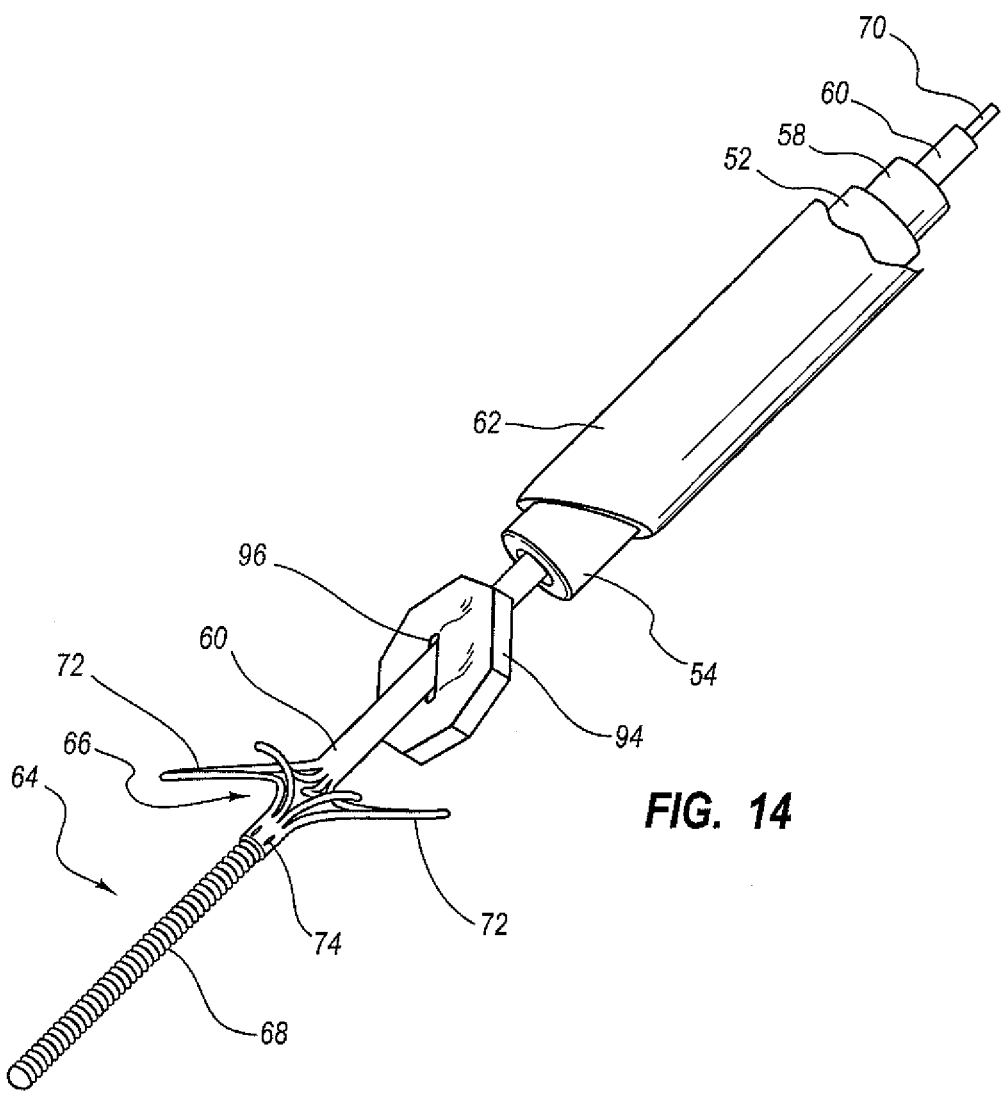

FIG. 14 shows yet another embodiment of a plug 94 that is shaped to prevent the plug 94 from moving away from the hole in the blood vessel. In this embodiment, the vessel locator tube 60 extends through a centrally located slot or hole 96 in the plug 94. The slot 96 is shaped to allow the plug 94 to pivot so that the plug 94 is at an angle relative to the vessel locator tube 60. This allows the plug 94 to fit inside the closure sheath 62. The plug 94 is deployed by advancing the plug 94 through the closure sheath 62 to the site of the puncture in the blood vessel. Once the closure sheath 62 is retracted and the plug 94 exposed, the plug 94 is pushed distally which causes the plug 94 to pivot to be perpendicular to the vessel locator tube 60 and the puncture tract to close the hole in the blood vessel.

Figure 15:
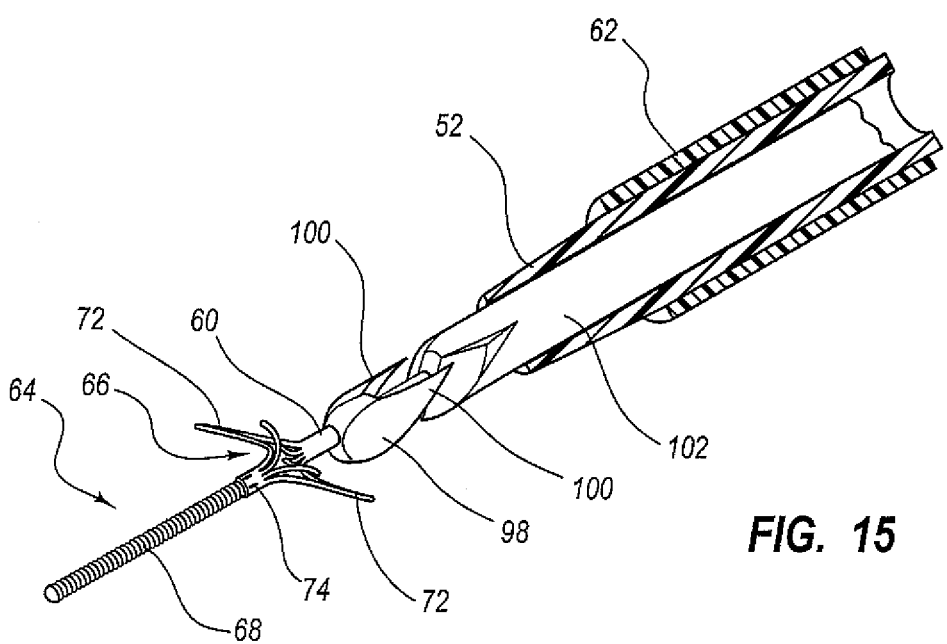

FIG. 15 shows yet another embodiment of a plug 98 that is shaped to prevent the plug 98 from moving away from the hole in the blood vessel. The plug 98 includes a plurality of projections or barbs 100 that extend outward from the plug 98. In this embodiment, the plug 98 is configured to mesh with the distal end of tube 102 so that the projections cannot catch the surrounding tissue of the puncture tact. The plug 98 may be deployed using the carrier tube 52. In this embodiment, the carrier tube 52 is tapered at the distal end so that it will catch the projections 100 and move the plug 98 distally from the tube 102 to expose the projections 100 to the surrounding tissue of the puncture tract. In the natural configuration of the plug 98 the bargs 100 project radially outward from the main body portion of the plug 98. Until the plug is to be deployed, the carrier tube 52 holds the barbs in a retracted state against the main body portion of the plug 98. Once in place, the vessel locator tube 60 may be withdrawn through the hole in the plug 98.

It should be appreciated that the embodiments of the plugs shown herein may be made of any suitable material. In one embodiment, the plugs are made of bioabsorbable materials such as PGA (poly glycolic acid), PLA (poly lactic acid), PCL (polycaprolactone), copolymers thereof, or variants or derivatives thereof. In another embodiment, the plugs may have an appreciably stable shape in the presence of bodily fluids so that the projections on and/or shape of the plugs are sufficient to contact the surrounding tissue in the puncture tract and hold the plugs in place.

Turning back to FIGS. 2-3, the tamper tube 58 may be used to tamp or compress a sealing material 56 against the plug 54. As shown, the sealing material 56 has a pre-formed shape and may be concentrically disposed around locator tube 60 (in cross section), as shown in FIG. 2. Alternatively, sealing material 56 may be positioned on one side of locator tube 60 so that the sealing material 56 forms a generally c-shaped configuration (in cross section), as shown in FIG. 3, with the material forming an apex 57 about an axis that is parallel to the central axis of locator tube 60.

Tamper tube 58 compresses the sealing material 56 relative to the plug 54. The tamping action serves to push the sealing material 56 radially outward into the tissue of the puncture tract. This helps to hold the sealing material 56 and the plug 54 in place as well as to further seal the puncture tract to prevent blood from leaking out.

Figure 8:
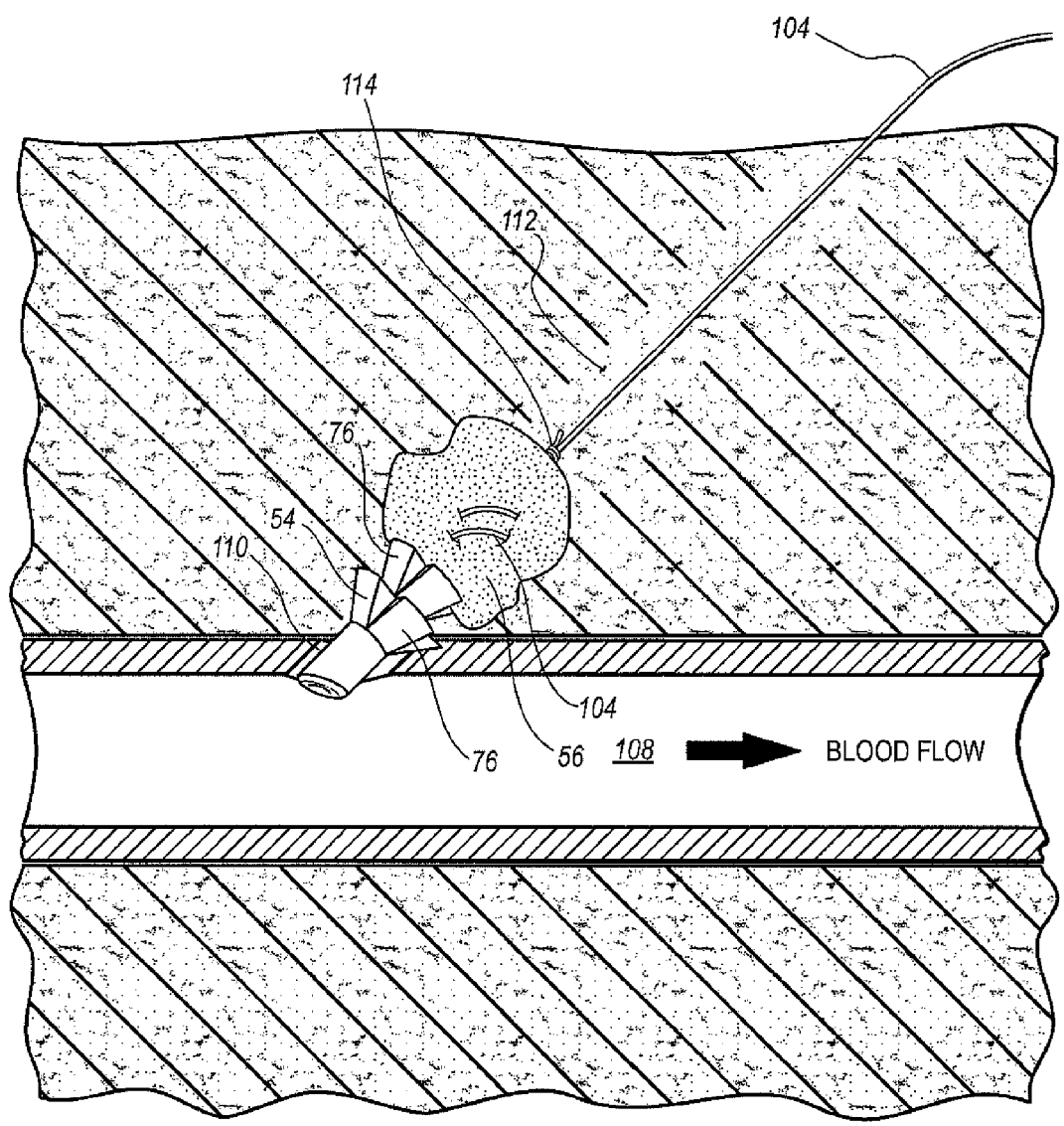
FIG. 8 shows the vascular closure device after the plug and sealing material has been deployed.

A suture or filament 104 may be used to hold the plug 54 and the sealing material 56 together. A slip knot 114 (FIG. 8) may be used to hold the sealing material 56 in a compressed state. At least FIG. 8 shows the sealing material 56 anchored in the puncture tract at least in part by connection of the sealing material 56 to the plug 54 with the suture 104. Referring back to FIG. 2, the vascular closure device 50 is configured to deploy the sealing material 56 adjacent to the hole in the blood vessel. In one embodiment, the sealing material 56 may be configured to swell when it contacts blood to further assist in closing the hole. The sealing material 56 may be any suitable material such as collagen or glycerol monooleate. Also, the sealing material 56 may be tapered at the distal end so that the sealing material fits into the hole in the blood vessel better. The distal end of the sealing material may have any suitable angle. It should be appreciated that the suture 104 may be unnecessary in those embodiments where glycerol monooleate or similar materials are used.

For those embodiments that use the suture 104, the plug 54 may include a transverse hole or lumen 106 sized to receive the suture 104. The suture 104 extends through the plug 54 and the sealing material 56. In the embodiment shown in FIGS. 2-3, the suture 104 passes through multiple holes in the sealing material 56 in a distal direction, through the transverse hole 106 in the plug 54, and back through more holes in the sealing material 56 in a proximal direction. As mentioned, a slip knot 114 (FIG. 8) may be provided on one end of the suture 104 above the sealing material 56 so that a loop is formed around the plug 54 and the sealing material 56. The other end of the suture 104 may extend proximally from the sealing material 56 through the tamper tube 58 to the proximate end of the vascular closure device 50. The suture 104 may be tightened by pulling on the suture at the proximate end of the vascular closure device 50 which tightens a slipknot of the suture in a known manner.

A method of closing a hole 110 in a blood vessel 108 using the vascular closure device 50 is described in connection with FIGS. 4-8. Initially, the procedural sheath is exchanged for the closure sheath 62. This exchange of the procedural sheath for the closure sheath 62 may not be required depending upon the sizing of the vascular closure device 50. This is done by placing a guidewire through the procedural sheath and into the blood vessel 108. The procedural sheath is then withdrawn from the body while holding digital pressure on the blood vessel 108, upstream from the sheath, and while holding the guidewire in place. Next, a closure dilator is placed within the closure sheath 62 and the distal tapered end of the closure dilator is back-loaded onto the guidewire. The closure dilator and the closure sheath 62 are advanced together distally over the guidewire, through the puncture or tissue tract 112, and into the blood vessel 108.

In one embodiment, the closure sheath 62 includes a distal side hole (not shown) near the distal end of the closure sheath 62. The closure dilator also includes a distal side hole that is configured to align with the distal side hole in the closure sheath 62 when the closure dilator is positioned in the closure sheath 62. The closure dilator also has a proximal side hole at the proximal end of the closure dilator that is in fluid communication with the distal side hole of the closure dilator and the closure sheath. In one embodiment, the distal and proximal side holes may be fluidly connected by way of a dedicated lumen or bore. In another embodiment, the distal and proximal side holes may be fluidly connected by the central lumen of the closure dilator that the guidewire is positioned in.

The side holes in the closure sheath 62 and the closure dilator are provided to allow blood to flash back when the closure sheath 62 is correctly positioned in the blood vessel 108. Once blood flows out the proximal side hole of the closure dilator, the user pulls the closure sheath 62 in a proximal direction until the blood flow just stops. The closure sheath 62 is now placed in the correct position to continue the procedure. The next step is to withdraw the closure dilator and the guidewire while holding the closure sheath 62 in place.

The closure sheath 62 is sized to slidably receive the vascular closure device 50 therein. The distal end of the closure sheath 62 is tapered so that the tip will align with the lengthwise axis of the blood vessel 108 when the closure sheath 62 is inserted through the puncture tract 112 at an angle of about 30-45 degrees to the vessel axis.

After the closure sheath 62 is in place, the vascular closure device 50 is introduced into the proximal end of the closure sheath 62. The vascular closure device 50 may be configured to advance until it snaps, locks, or otherwise mates together with the carrier tube 62. In this position, the distal end 64 of the vascular closure device 50 extends out of the distal end of the closure sheath 62 and into the blood vessel 108. It should be noted that the vascular closure device 50 and the closure sheath 62 may be configured so that when they are coupled together, the distal end 64 extends into the blood vessel 108 a predetermined amount.

Figure 4:
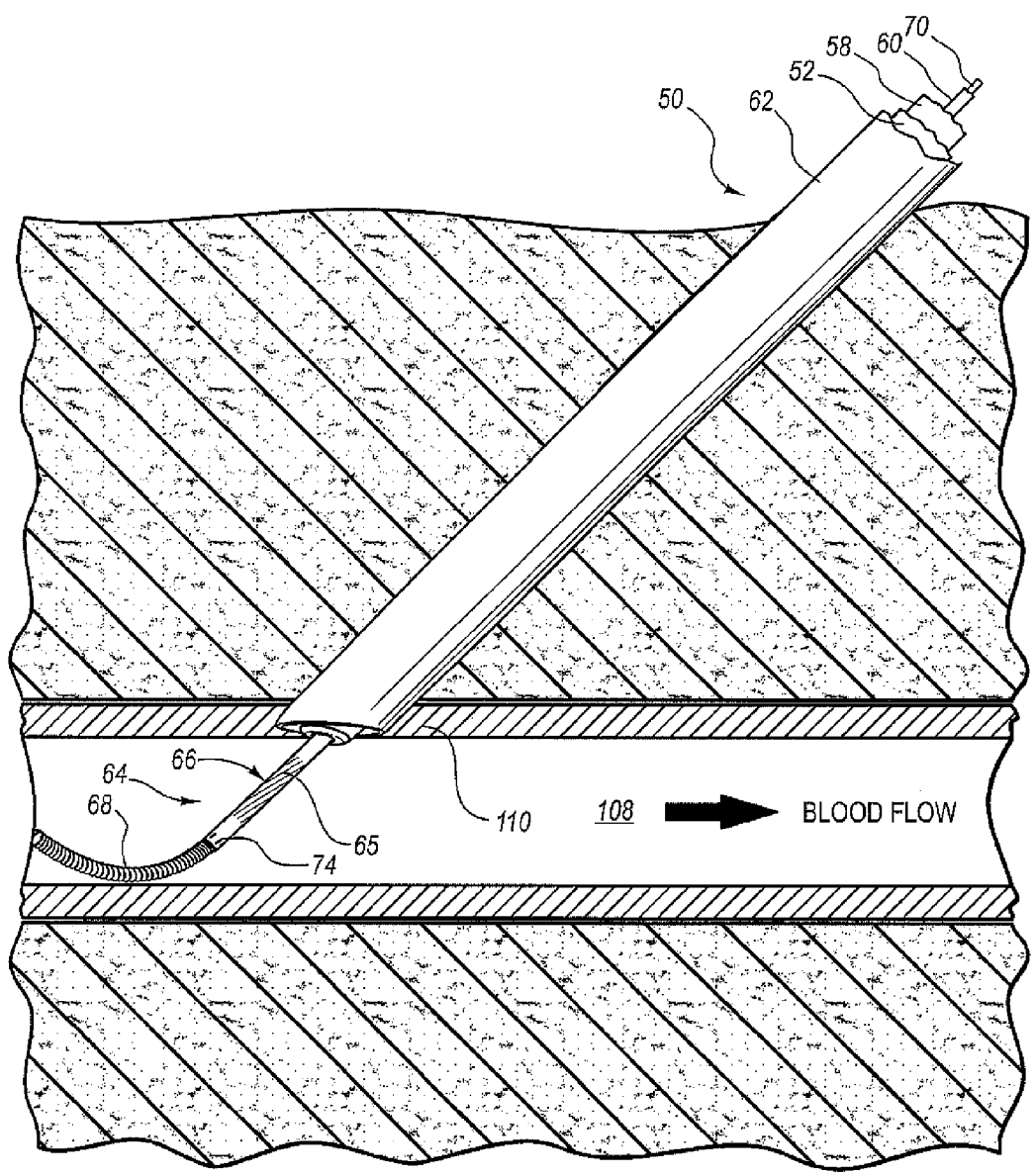
FIG. 4 shows the vascular closure device inserted into a blood vessel.
Figure 5:
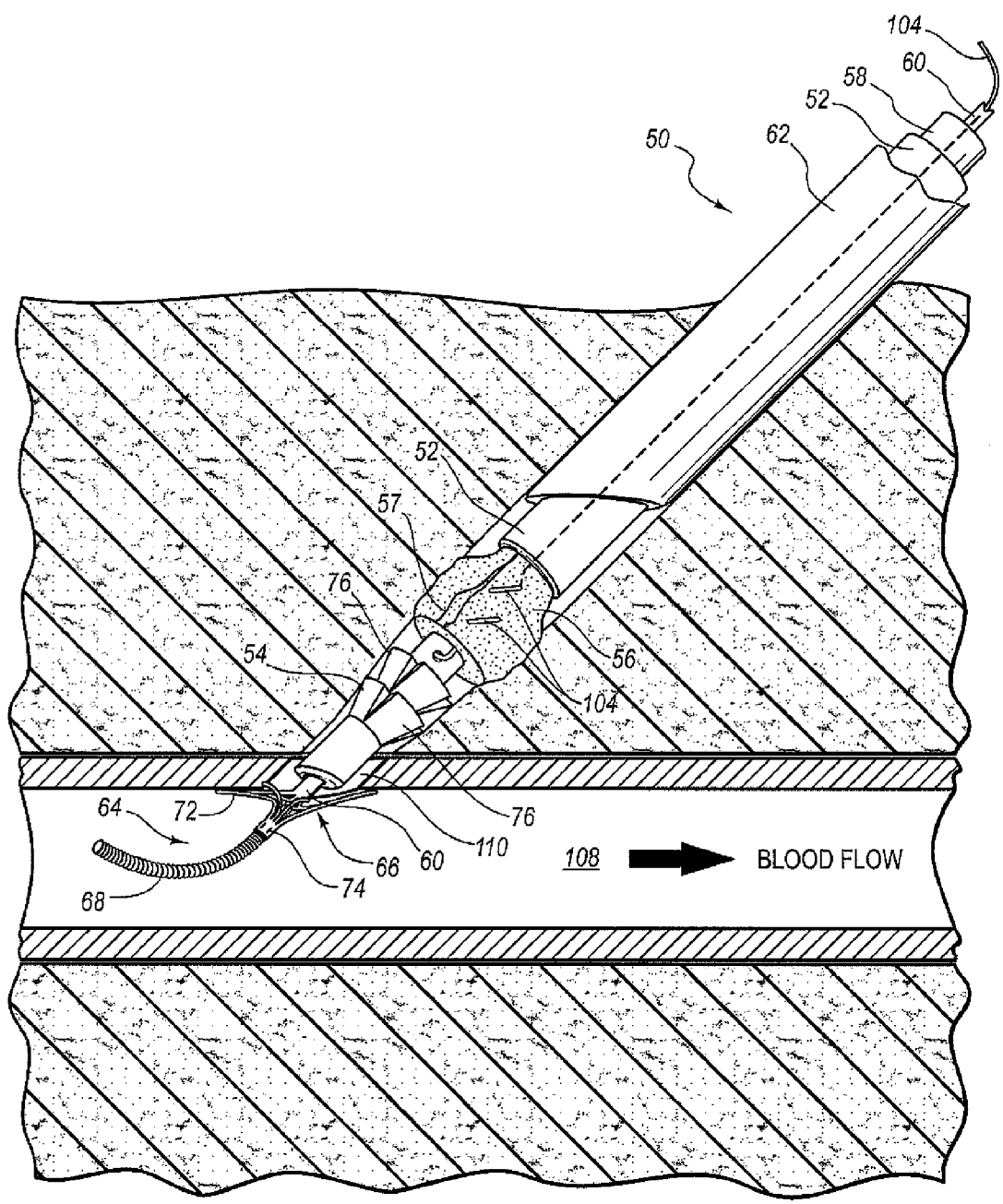
FIG. 5 shows the vascular closure device inserted into the blood vessel with a vessel locating member in an expanded position and the plug in a deployed position.

FIG. 4 shows the vessel locating member 66 in position in the blood vessel 108. The vessel locating member 66 is expanded by pulling the core wire 70 proximally as explained above. FIG. 5 shows the vessel locating member 66 in the expanded configuration. The closure sheath 62 and the vascular closure device 50 are drawn away from the patient until the vessel locating member 66 contacts the vessel wall at the puncture site.

Now that the vessel locating member 66 and the plug 54 are in position, the closure sheath 62 and the carrier tube 52 are withdrawn to expose the plug 54 and the sealing material 56 to the tissue puncture tract 112. The sealing material, which may include a collagen sponge, is now exposed to the puncture tract and starts to absorb blood and swell. It should be appreciated that the vascular closure device 50 may be configured to not use the sealing material 56 and only use the plug 54. The plug 54 may adequately close the hole 110 by itself.

Figure 7:
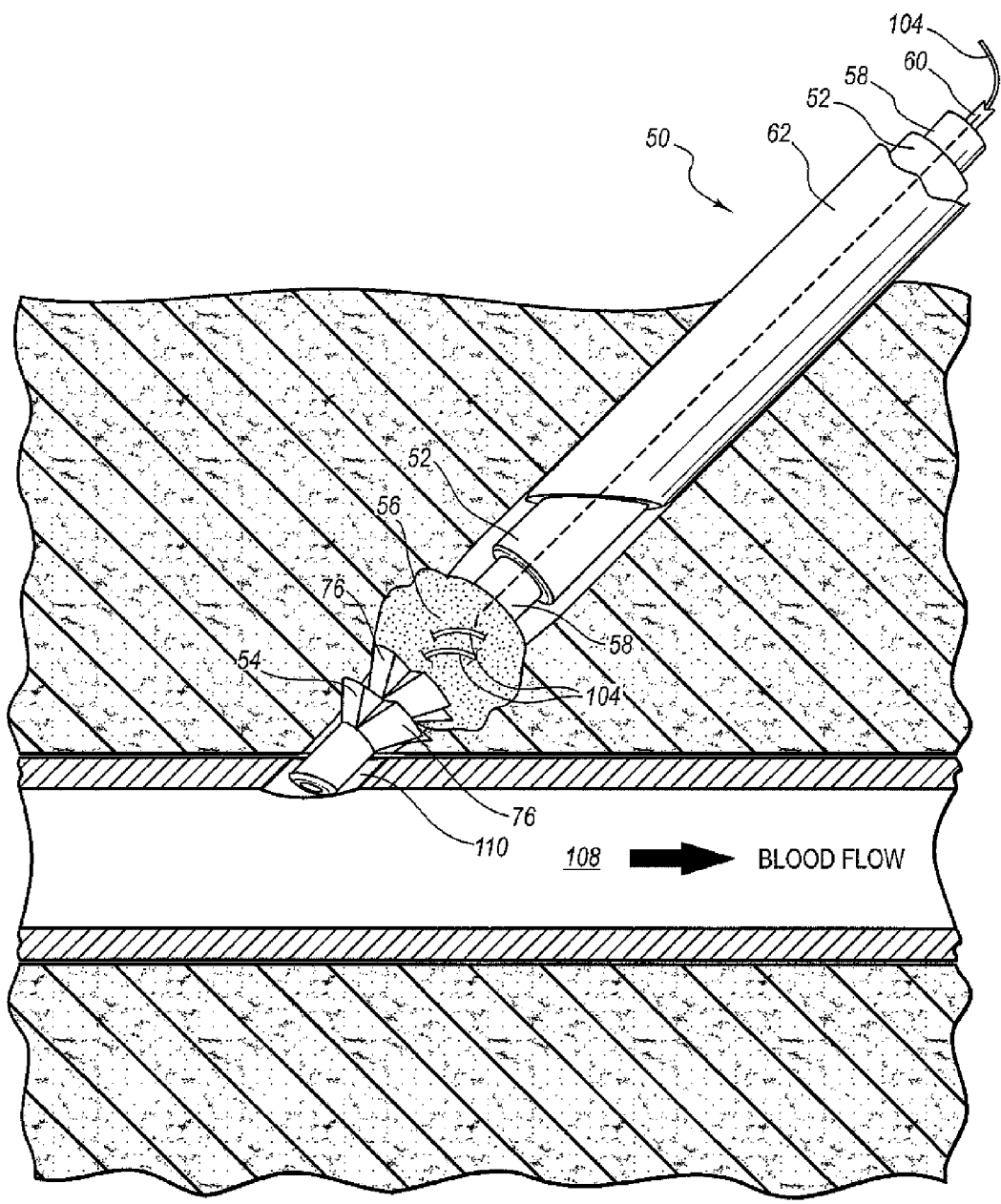
FIG. 7 shows the vascular closure device after the plug and sealing material has been deployed but before the vascular closure device has been removed from the puncture tract.

Now that the sealing material 56 has been deployed, the next step is to tamp it with the tamper tube 58. This is accomplished by pushing the tamper tube 58 distally into the sealing material 56 as shown in FIG. 6. The tamper tube 58 compresses the sealing material 56 against the plug 54, the wall of the blood vessel 108, and the vessel locating member 66. The vessel locating member 66 prevents the sealing material 56 and/or the plug 54 from being pushed inside the blood vessel 108 during the tamping procedure. FIG. 7 shows the sealing material 56 after the tamper tube 58 has been retracted.

The suture 104 is tightened to hold the sealing material 56 in a compressed state. The suture is tightened by pulling it in a proximal direction to tighten the slip knot. At this point, the sealing material 56 and the plug 54 have been deployed and the only remaining steps are to remove the closure sheath 62 and the vascular closure device 50.

It should be appreciated that certain sealing materials 56 such as glycerol monooleate and the like may not require tamping and/or the use of the suture 104. Since these materials melt or form a gel at bodily temperatures, they initially flow against the proximal end of the plug 54. As these materials interact with body fluids they take on a different form that causes them to swell and further seal the puncture tract 112.

The first step in removing the vascular closure device 50 is to contract or collapse the vessel locating member 66 and remove the vessel locator tube 60 from the vascular closure device 50. The vessel locating member 66 is contracted by moving the core wire 70 distally as explained above. At this point, the vessel locator tube 60 may be pulled out of the proximal end of the vascular closure device 50. As the vessel locator tube 60 passes through the sealing material 56, the sealing material 56 swells to fill the gap where the vessel locator tube 60 used to be. The hole in the blood vessel 108 is now sealed by clotting action and the swelling of the sealing material 56 against the walls of puncture tract 112. The plug 54 and the sealing material 56 are not disturbed by the removal of the vessel locator tube 60 since the vessel locator tube 60 and the coiled spring 68 are smaller than the lumens through the plug 54 and the sealing material 56.

The remainder of the vascular closure device 50 can be removed by pulling it proximally out of the puncture tract 112. The suture 104 may be cut at any time. If the suture 104 still extends out of the skin, the user can cut again by compressing the skin and severing the suture 104 at a point below the surface of the skin. The closure procedure is now complete and the sealing material 56, suture 104, and the plug 54 will be absorbed by the body in about 90 days or less.

It should be appreciated that the embodiments disclosed have many components and the methods described have many steps for operation and use. It is anticipated that the number of components and steps could be altered considerably (e.g., remove the second tube 74, etc.) without departing from the broad scope of what is described herein. For example the steps of tamping and tensioning the suture 104 could be combined into one step.

Illustrative Embodiments

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.) from the particular embodiments explained below. Accordingly, any combination of any of the subject matter described herein is contemplated.

According to one embodiment, a method of closing a hole in a blood vessel comprises: locating a wall of the blood vessel adjacent to the hole; and positioning a plug outside of the blood vessel and adjacent to the hole, the plug being shaped to prevent the plug from moving away from the blood vessel; wherein the plug is bioabsorbable and has an appreciably stable shape in the presence of bodily fluids. The plug may include a plurality of projections that are configured to contact surrounding tissue to prevent the plug from moving away from the blood vessel. The plug may include a plurality of barbs that are configured to contact surrounding tissue to prevent the plug from moving away from the blood vessel. The plug may include a rod that moves inside a sleeve, wherein the rod may include a plurality of projections that extend through a corresponding plurality of holes in the sleeve to contact surrounding tissue to prevent the plug from moving away from the blood vessel. Locating the wall of the blood vessel may include inserting a vessel locating member through the hole in the blood vessel, expanding the vessel locating member, and moving the vessel locating member into contact with the wall of the blood vessel. The vessel locating member may include a tube having a wall with a plurality of cuts in it, the wall of the tube being configured to expand where the plurality of cuts are located when the tube is compressed. The vessel locating member may include a balloon. The method may comprise deploying a sealing material adjacent to the plug.

According to another embodiment, a method of closing a hole in a blood vessel comprises: positioning a plug outside of the blood vessel to close the hole in the blood vessel; wherein the plug is bioabsorbable and has an appreciably stable shape in the presence of bodily fluids. The plug may be shaped to prevent the plug from moving away from the blood vessel. The plug may include a plurality of projections that are configured to contact surrounding tissue to prevent the plug from moving away from the blood vessel. The plug may include a plurality of barbs that are configured to contact surrounding tissue to prevent the plug from moving away from the blood vessel. The plug may include a rod that moves inside a sleeve, wherein the rod may include a plurality of projections that extend through a corresponding plurality of holes in the sleeve to contact surrounding tissue and thereby prevent the plug from moving away from the blood vessel. The method may comprise deploying a sealing material adjacent to the plug. The method may comprise compressing the sealing material and the plug together. The method may comprise holding the sealing material and the plug together using a suture.

According to another embodiment a method of closing a hole in a blood vessel comprises: positioning a plug outside of the blood vessel to close the hole in the blood vessel; wherein the plug includes a plurality of projections that are configured to contact surrounding tissue to prevent the plug from moving away from the blood vessel. The plug may include a plurality of barbs that are configured to contact surrounding tissue to prevent the plug from moving away from the blood vessel. The plug may include a rod that moves inside a sleeve, wherein the rod may include a plurality of projections that extend through a corresponding plurality of holes in the sleeve to contact surrounding tissue and thereby prevent the plug from moving away from the blood vessel. The method may comprise deploying a sealing material adjacent to the plug. The method may comprise locating a wall of the blood vessel adjacent to the hole.

According to another embodiment, a vascular closure device comprises: a vessel locating member configured to be inserted through a hole in a blood vessel to locate the position of a wall of the blood vessel that is adjacent to the hole; and a plug configured to be deployed outside of the blood vessel adjacent to the hole, the plug being shaped to prevent the plug from moving away from the blood vessel; wherein the plug is bioabsorbable and has an appreciably stable shape in the presence of bodily fluids. The plug may include a plurality of projections that are configured to contact surrounding tissue to prevent the plug from moving away from the blood vessel. The plug may include a plurality of barbs that are configured to contact surrounding tissue to prevent the plug from moving away from the blood vessel. The plug may include a rod that moves inside a sleeve, wherein the rod may include a plurality of projections that extend through a corresponding plurality of holes in the sleeve to contact surrounding tissue and thereby prevent the plug from moving away from the blood vessel. The vessel locating member may be configured to move between an expanded configuration and a contracted configuration. The vessel locating member may include a tube having a wall with a plurality of cuts in it, the wall of the tube being configured to expand where the plurality of cuts are located when the tube is compressed. The vessel locating member may include a balloon.

According to another embodiment, a vascular closure device comprises: a vessel locating member configured to locate a wall of a blood vessel that is adjacent to a hole in the blood vessel; a plug configured to be deployed outside of the blood vessel adjacent to the hole in the blood vessel, the plug being shaped to prevent the plug from moving away from the blood vessel; and a sealing material configured to be deployed adjacent to the plug, the sealing material being positioned outside of the blood vessel; wherein the plug is bioabsorbable. The plug may include a plurality of projections that are configured to contact surrounding tissue to prevent the plug from moving away from the blood vessel. The plug may include a plurality of barbs that are configured to contact surrounding tissue to prevent the plug from moving away from the blood vessel. The plug may include a rod that moves inside a sleeve, wherein the rod may include a plurality of projections that extend through a corresponding plurality of holes in the sleeve to contact surrounding tissue and thereby prevent the plug from moving away from the blood vessel. The vascular closure device may be configured so that the plug and the vessel locating member are positioned near each other so that when the vessel locating member is in contact with an interior surface of the wall of the blood vessel, the plug is adjacent to the wall on the outside of the blood vessel. The vessel locating member may be configured to move between an expanded configuration to allow the vessel locating member to contact the interior surface of the wall of the blood vessel and a contracted configuration to allow the vessel locating member to pass through the hole in the blood vessel. The sealing material may include collagen. The vascular closure device may comprise a suture configured to hold the sealing material and the plug together. The vascular closure device may comprise a tamper member configured to move the sealing material toward the plug.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9974, and so forth).

What is claimed is:

1. A vascular closure device comprising:
   a vessel locating member configured to be inserted through a hole in a blood vessel when in a retracted position and being expandable within the blood vessel to locate the position of a wall of the blood vessel that is adjacent to the hole;
   a plug configured to be deployed outside of the blood vessel adjacent to the hole and proximal of the vessel locating member within a tissue tract, the plug being shaped to prevent the plug from moving away from the blood vessel within the tissue tract;
   a sealing material configured to be positioned within the tissue tract proximal of and in contact with the plug, the sealing material having a pre-formed shape;
   a tamping member positioned proximal of the sealing material and operable to directly contact and compact the sealing material into a compacted position against the plug prior to removal of the vessel locating member;
   a suture connecting the sealing material to the plug, the suture holding the sealing material in the compacted position;
   wherein the plug is bioabsorbable and has an appreciably stable shape in the presence of bodily fluids;
   wherein the vessel locating member extends through the plug and the sealing material.

2. The vascular closure device of claim 1 wherein the plug includes a plurality of projections that are configured to contact surrounding tissue to prevent the plug from moving away from the blood vessel.

3. The vascular closure device of claim 1 wherein the plug includes a plurality of barbs that are configured to contact surrounding tissue to prevent the plug from moving away from the blood vessel.

4. The vascular closure device of claim 1 wherein the plug includes a rod that moves inside a sleeve, wherein the rod includes a plurality of projections that extend through a corresponding plurality of holes in the sleeve to contact surrounding tissue and thereby prevent the plug from moving away from the blood vessel.

5. The vascular closure device of claim 1 wherein the vessel locating member includes a tube having a wall with a plurality of cuts in it, the wall of the tube being configured to expand where the plurality of cuts are located when the tube is compressed.

6. The vascular closure device of claim 1 wherein the vessel locating member includes a balloon.

7. The vascular closure device of claim 1 wherein the sealing material is configured to be deployed adjacent to the plug outside of the blood vessel.

8. The vascular closure device of claim 1, wherein the plug has a first portion configured to be deployed outside of the blood vessel adjacent to the hole, and a second portion configured to be positioned within the hole.

9. The vascular closure device of claim 1, wherein the plug comprises at least one hole sized to receive the suture, and the sealing material includes multiple holes sized to receive the suture.

10. The vascular closure device of claim 1, wherein the plug includes an end surface that is angled to be flush with an interior wall surface of the blood vessel.

11. The vascular closure device of claim 1 wherein the tamping member comprises a tamper tube configured to compact the sealing material distally against a proximal end of the plug.

12. The vascular closure device of claim 1, further comprising a carrier tube defining a lumen sized to retain the plug and sealing material, the carrier tube being retractable to expose the plug and sealing material adjacent to the blood vessel.

13. A vascular closure device comprising:
- a vessel locating member configured to be insertable through a hole in a blood vessel when in a retracted position and being expandable within an interior of the blood vessel;
- a plug configured to be positioned outside of the blood vessel interior at least partially positioned in a tissue tract at a location proximal of the vessel locating member, the plug having at least one barb member directed proximally to contact the tissue tract to resist moving away from the blood vessel within the tissue tract;
- a sealing material configured to be positioned within the tissue tract adjacent to and proximal of the plug, the sealing material having a pre-formed shape;
- a tamping member positioned proximal of the sealing material and operable to directly contact and compact the sealing material into a compacted position against the plug prior to removal of the vessel locating member;
- a suture connecting the sealing material to the plug, the suture holding the sealing material in the compacted position;
- wherein the vessel locating member extends through the plug and the sealing material.

14. The vascular closure device of claim 13, wherein the plug includes a first portion configured to be positioned in the hole, and a second portion configured to be positioned in the tissue tract, the at least one barb member being mounted to the second portion.

15. The vascular closure device of claim 13, wherein the plug has a plurality of barb members arranged in a plurality of parallel rows extending around a circumference of the plug.

16. The vascular closure device of claim 13, wherein the plug includes a rod that moves inside a sleeve, wherein the rod includes a plurality of barbs that extend through a corresponding plurality of holes in the sleeve to contact the tissue tract to resist moving away from the blood vessel.

17. The vascular closure device of claim 13, wherein the plug includes an end surface that is angled to be flush with an interior wall surface of the blood vessel.

18. The vascular closure device of claim 13, wherein the tamping member is configured to compact the sealing material distally against a proximal end of the plug.

* * * * *